US00PP25770P2

(12) United States Plant Patent
Shibamichi

(10) Patent No.: US PP25,770 P2
(45) Date of Patent: Aug. 4, 2015

(54) ***RHAPHIOLEPSIS* PLANT NAMED 'SPG-3-003'**

(50) Latin Name: *Rhaphiolepsis indica*
Varietal Denomination: sPg-3-003

(71) Applicant: Akira Shibamichi, Kawaguchi (JP)

(72) Inventor: Akira Shibamichi, Kawaguchi (JP)

(73) Assignee: Southern Plant Group, Atlanta, GA (US)

( * ) Notice: Subject to any disclaimer, the term of this patent is extended or adjusted under 35 U.S.C. 154(b) by 109 days.

(21) Appl. No.: 13/987,777

(22) Filed: Aug. 31, 2013

(51) Int. Cl.
*A01H 5/12* (2006.01)

(52) U.S. Cl.
USPC ..... Plt./254

(58) Field of Classification Search
USPC ..... Plt./254
See application file for complete search history.

*Primary Examiner* — Anne Grunberg
(74) *Attorney, Agent, or Firm* — C. A. Whealy

(57) ABSTRACT

A new and distinct cultivar of *Rhaphiolepis* plant named 'sPg-3-003', characterized by its compact and upright globular plant habit; freely branching habit, dense and bushy plant form; dark red-colored developing leaves; numerous flowers with white-colored petals and red purple-colored sepals; and good container and garden performance.

3 Drawing Sheets

Botanical designation: *Rhaphiolepis indica.*
Cultivar denomination: 'sPg-3-003'.

BACKGROUND OF THE INVENTION

The present invention relates to a new and distinct *Rhaphiolepis* plant, botanically known as *Rhaphiolepis indica* and hereinafter referred to by the name 'sPg-3-003'.

The new *Rhaphiolepis* plant is a naturally-occurring whole plant mutation of an unnamed proprietary selection of *Rhaphiolepis indica*, not patented. The new *Rhaphiolepis* plant was discovered and selected by the Inventor as a single plant within a population of plants of the unnamed proprietary selection in a controlled nursery environment in Kawaguchi City, Japan in 2002.

Asexual reproduction of the new *Rhaphiolepis* plant by vegetative cuttings in a controlled environment in Kawaguchi City, Japan since the summer of 2002 has shown that the unique features of this new *Rhaphiolepis* plant are stable and reproduced true to type in successive generations.

SUMMARY OF THE INVENTION

Plants of the new *Rhaphiolepis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'sPg-3-003'. These characteristics in combination distinguish 'sPg-3-003' as a new and distinct *Rhaphiolepis* plant:

1. Compact and upright globular plant habit.
2. Freely branching habit, dense and bushy plant form.
3. Dark red-colored developing leaves.
4. Numerous flowers with white-colored petals and red purple-colored sepals.
5. Good container and garden performance.

Plants of the new *Rhaphiolepis* can be compared to plants of the parent selection. Plants of the new *Rhaphiolepis* differ from plants of the parent selection in developing leaf color as plants of the parent selection have green-colored developing leaves. In addition, plants of the new *Rhaphiolepis* are more upright than and not as outwardly spreading as plants of the parent selection.

Plants of the new *Rhaphiolepis* can also be compared to plants of *Rhaphiolepis indica* 'Dwarf Pink', not patented. In side-by-side comparisons, plants of the new *Rhaphiolepis* differed primarily from plants of 'Dwarf Pink' in developing leaf color as plants of 'Dwarf Pink' had green-colored developing leaves. In addition, plants of the new *Rhaphiolepis* were more upright than and not as outwardly spreading as plants of 'Dwarf Pink'.

BRIEF DESCRIPTION OF THE PHOTOGRAPHS

The accompanying colored photographs illustrate the overall appearance of the new *Rhaphiolepis* plant showing the colors as true as it is reasonably possible to obtain in colored reproductions of this type. Colors in the photographs may differ slightly from the color values cited in the detailed botanical description which accurately describe the colors of the new *Rhaphiolepis* plant.

The photograph on the first sheet is a side perspective view of a typical flowering plant of 'sPg-3-003'.

The photograph on the second sheet is a close-up view of a typical flowering plant of 'sPg-3-003'.

The photograph on the third sheet is a close-up view of typical flowers of 'sPg-3-003'.

DETAILED BOTANICAL DESCRIPTION

The aforementioned photographs and following observations, measurements and values describe plants grown during the spring in three-gallon containers in an outdoor nursery in El Campo, Tex. and under cultural practices typical of commercial *Rhaphiolepis* production. During the production of the plants, day temperatures averaged 27° C. and night temperatures averaged 14° C. Plants were two years old when the photographs and the description were taken. In the description, color references are made to The Royal Horticultural Society Colour Chart, 1995 Edition, except where general terms of ordinary dictionary significance are used.

Botanical classification: *Rhaphiolepis indica* 'SPg-3-003'.

Parentage: Naturally-occurring whole plant mutation of an unnamed proprietary selection of *Rhaphiolepis indica*, not patented.

Propagation:

*Type*.—By vegetative cuttings.

*Time to initiate roots, summer*.—About four to six weeks at temperatures about 29° C.

*Time to produce a rooted young plant, summer*.—About two to three months at temperatures about 29° C.

*Root description*.—Medium in thickness, fibrous; brown in color.

*Rooting habit*.—Moderately freely branching; medium density.

Plant description:

*Plant and growth habit*.—Perennial shrub; compact and upright globular plant habit; moderately vigorous growth habit; freely branching habit with lateral branches potentially developing at every node; dense and bushy plant form.

*Plant height*.—About 91.44 cm.

*Plant diameter* (*area of spread*).—About 91.44 cm.

Lateral branch description:

*Length*.—About 53.34 cm.

*Diameter*.—About 1.48 cm.

*Internode length*.—About 1.5 cm.

*Aspect*.—About 30° from vertical.

*Strength*.—Strong; flexible.

*Texture*.—Pubescent.

*Color, immature*.—Close to 183A.

*Color, mature*.—Close to 200C.

Leaf description:

*Arrangement*.—Alternate, single.

*Length*.—About 4.5 cm.

*Width*.—About 1.5 cm to 1.8 cm.

*Shape*.—Oval.

*Apex*.—Acute.

*Base*.—Attenuate.

*Margin*.—Slightly dentate.

*Texture, upper and lower surfaces*.—Smooth, glabrous; leathery.

*Venation pattern*.—Pinnate; arcuate.

*Color*.—Developing leaves, upper surface: Close to 187A. Developing leaves, lower surface: Close to 183C. Fully expanded leaves, upper surface: Close to 147A; venation, close to 147B. Fully expanded leaves, lower surface: Close to 147B; venation, close to 147B.

*Petioles*.—Length: About 5 mm. Diameter: About 1.5 mm. Texture, upper and lower surfaces: Smooth, glabrous. Color, upper and lower surfaces: Close to 147B.

Flower description:

*Flower arrangement and flowering habit*.—Single flowers arranged in terminal and axillary racemes; freely flowering habit; flowers face upright to outwardly.

*Natural flowering season*.—Early flowering habit, plants of the new Rhaphiolepis begin flowering in March and April in Texas; flowers not persistent.

*Fragrance*.—None detected.

*Flower diameter*.—About 1.4 cm.

*Flower length* (*height*).—About 9 mm.

*Flower buds*.—Length: About 8 mm to 9 mm. Diameter: About 4 mm to 5 mm. Shape: Ovoid. Color: Close to 155A; sepals, close to 59B.

*Petals*.—Arrangement: Typically five petals in a single whorl. Length: About 8 mm. Width: About 5 mm. Shape: Ovate. Apex: Acute. Base: Obtuse. Margin: Mostly entire; occasionally notched. Texture: Smooth, glabrous. Color: When opening, upper and lower surfaces: Close to 155A. Fully opened, upper and lower surfaces: Close to 155A.

*Sepals*.—Arrangement: Typically five sepals in a single whorl. Length: About 3 mm. Width: About 2 mm. Shape: Lanceolate. Apex: Acute. Base: Fused. Margin: Entire. Texture, upper and lower surfaces: Pubescent. Color, upper surface: Close to 60A. Color, lower surface: Close to 59B.

*Peduncles*.—Length: About 3 cm. Diameter: About 2 mm. Strength: Strong, flexible. Texture: Pubescent. Color: Close to 146C blushed with close to 183C.

*Pedicels*.—Length: About 2 mm to 5 mm. Diameter: About 1.5 mm. Strength: Strong, flexible. Texture: Pubescent. Color: Close to 146C blushed with close to 183C.

*Reproductive organs*.—Androecium: Stamen number: About 16 per flower. Filament length: About 4 mm to 6 mm. Filament color: Close to 158C becoming closer to 53C with development. Anther shape: Double oval. Anther length: About 1 mm. Anther color: Close to 10C. Amount of pollen: Moderate. Pollen color: Close to 10A. Gynoecium: Pistil number: One per flower. Pistil length: About 5 mm. Style length: About 4 mm. Style color: Close to 150D. Stigma shape: Club-shaped. Stigma color: Close to 150D. Ovary color: Close to 150D.

*Seeds and fruits*.—Seed and fruit development have not been observed on plants of the new *Rhaphiolepis*.

Garden performance: Plants of the new *Rhaphiolepis* have been observed to have good garden performance and to tolerate wind, rain and temperatures ranging from about −12° C. to about 37° C.

Pathogen & pest resistance: Plants of the new *Rhaphiolepis* have not been observed to be resistant to pathogens and pests common to *Rhaphiolepis* plants.

It is claimed:

1. A new and distinct *Rhaphiolepis* plant named 'sPg-3-003' as illustrated and described.

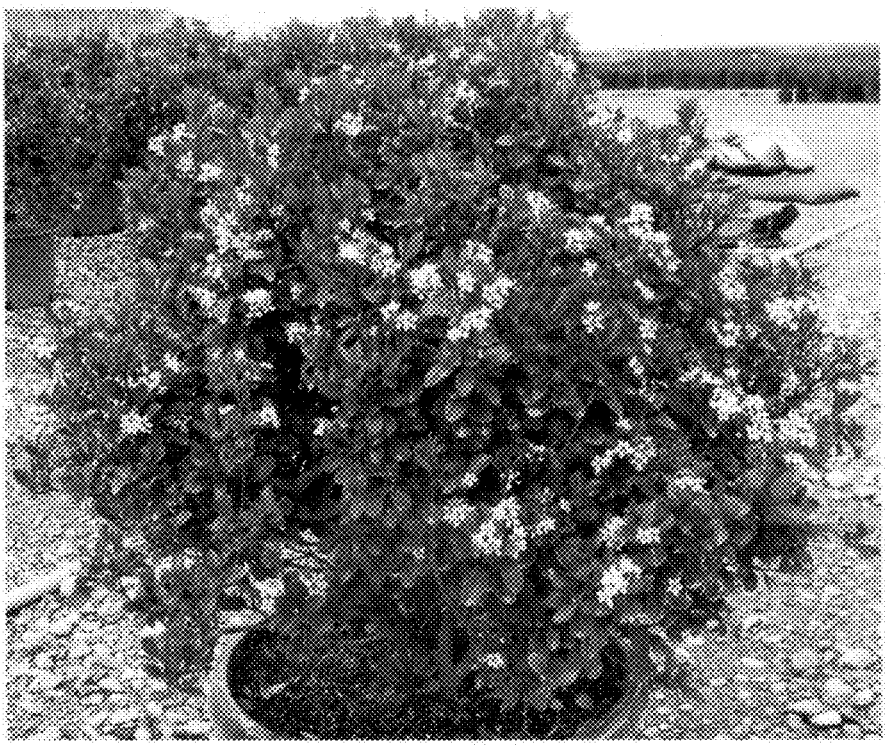

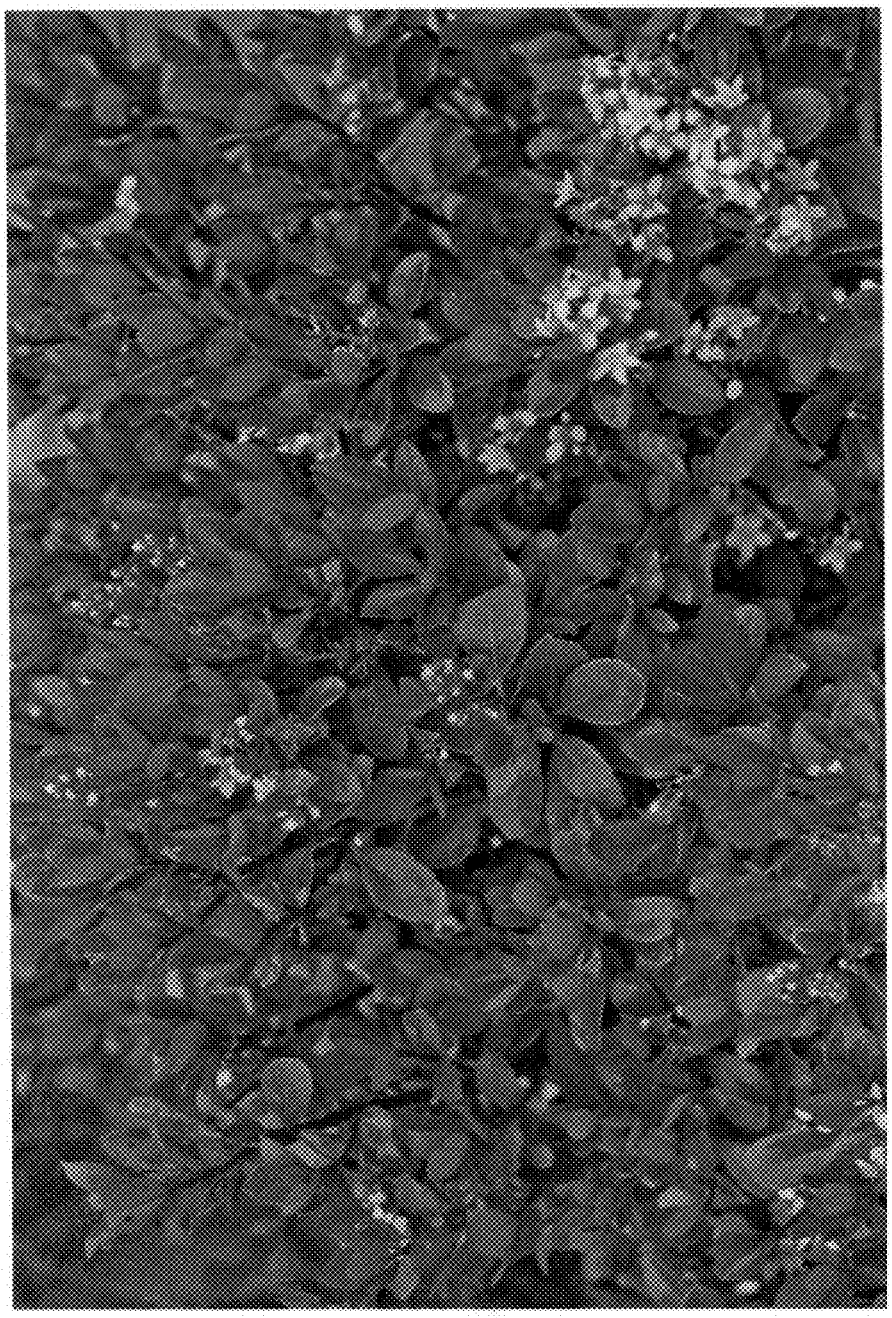

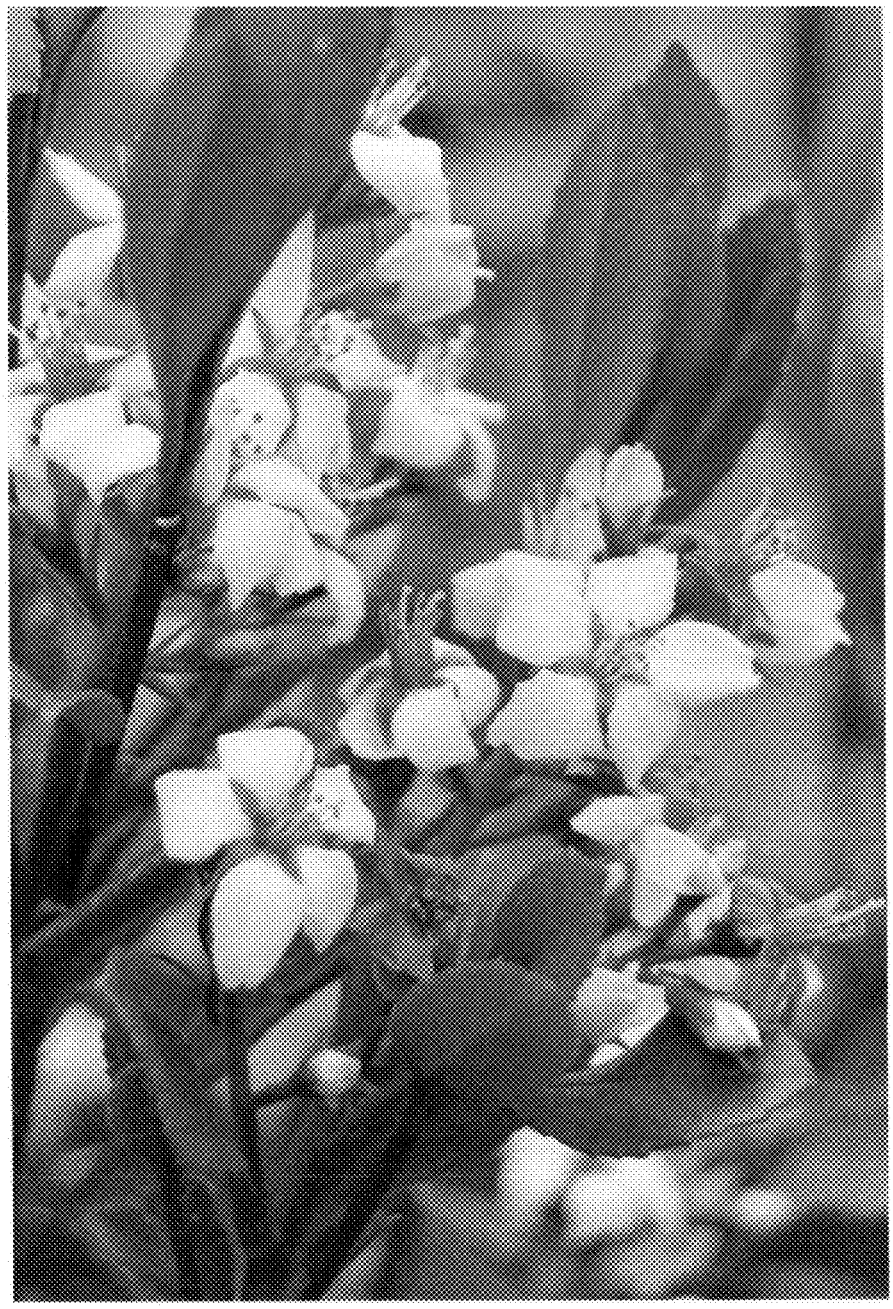

* * * * *